(12) United States Patent
Tegels et al.

(10) Patent No.: US 9,192,386 B2
(45) Date of Patent: Nov. 24, 2015

(54) BIOADHESIVE MIXING AND DELIVERY DEVICE AND METHODS

(71) Applicant: St. Jude Medical Puerto Rico LLC, Caguas, PR (US)

(72) Inventors: Zachary J. Tegels, Minneapolis, MN (US); Edward E. Parsonage, St. Paul, MN (US); Russell D. Terwey, St. Michael, MN (US); Martha Escobar, Jordan, MN (US); Timothy M. McGlinch, St. Paul, MN (US); Bernhard Kaeferlein, Champlin, MN (US); Troy T. White, Maple Grove, MN (US)

(73) Assignee: ST. JUDE MEDICAL PUERTO RICO LLC, Caguas, PR (US)

( * ) Notice: Subject to any disclaimer, the term of this patent is extended or adjusted under 35 U.S.C. 154(b) by 217 days.

(21) Appl. No.: 13/773,062

(22) Filed: Feb. 21, 2013

(65) Prior Publication Data

US 2014/0058441 A1  Feb. 27, 2014

Related U.S. Application Data

(60) Provisional application No. 61/693,052, filed on Aug. 24, 2013.

(51) Int. Cl.
*A61B 17/08* (2006.01)
*A61B 17/00* (2006.01)

(52) U.S. Cl.
CPC .............. *A61B 17/08* (2013.01); *A61B 17/0057* (2013.01); *A61B 2017/0065* (2013.01); *A61B 2017/00495* (2013.01)

(58) Field of Classification Search
CPC .............. A61B 17/08; A61B 17/0057; A61B 2017/0065
USPC ................. 606/191, 213, 214; 604/82, 93.01; 424/422, 423
See application file for complete search history.

(56) References Cited

U.S. PATENT DOCUMENTS

| | | |
|---|---|---|
| 6,830,756 B2 | 12/2004 | Hnojewyj |
| 6,874,657 B2 | 4/2005 | Metzner et al. |
| 7,516,872 B2 | 4/2009 | Boone et al. |
| 8,333,787 B2 | 12/2012 | Pipenhagen et al. |
| 8,506,592 B2 | 8/2013 | Killion et al. |
| 2004/0267308 A1 | 12/2004 | Bagaoisan et al. |
| 2010/0274129 A1* | 10/2010 | Hooven ........................ 600/435 |

(Continued)

OTHER PUBLICATIONS

U.S. Appl. No. 13/770,586, filed Feb. 19, 2013.

(Continued)

*Primary Examiner* — Victor Nguyen
(74) *Attorney, Agent, or Firm* — Holland & Hart

(57) ABSTRACT

A tissue puncture closure device includes a delivery member, a handle assembly, and a sealant cartridge. The delivery member includes a sealant lumen and is insertable into a tissue puncture. The handle assembly is mounted to a proximal end of the delivery member and includes a cartridge chamber and a plunger member. The sealant cartridge is insertable into the cartridge chamber. The sealant cartridge has at least first and second sealant chambers carrying at least first and second sealant components, respectively. Operation of the handle assembly ejects the first and second sealant components into the sealant lumen for delivery to the tissue puncture.

10 Claims, 11 Drawing Sheets

(56) References Cited

U.S. PATENT DOCUMENTS

| | | |
|---|---|---|
| 2011/0104280 A1* | 5/2011 | Hnojewyj .................... 424/486 |
| 2011/0166595 A1 | 7/2011 | Vidlund et al. |
| 2011/0282383 A1 | 11/2011 | Vidlund et al. |
| 2013/0006299 A1 | 1/2013 | Pipenhagen et al. |
| 2013/0190808 A1 | 7/2013 | Tegels et al. |
| 2013/0190812 A1 | 7/2013 | Vidlund |
| 2013/0190813 A1 | 7/2013 | Tegels et al. |

OTHER PUBLICATIONS

U.S. Appl. No. 13/770,714, filed Feb. 19, 2013.
PCT Notification of Transmittal of the International Search Report and the Written Opinion of the International Searching Authority, or the Declaration for International Application No. PCT/US2013/027054, mailed May 31, 2013 (11 pp.).
U.S. Appl. No. 13/772,384, filed Feb. 21, 2013.

* cited by examiner

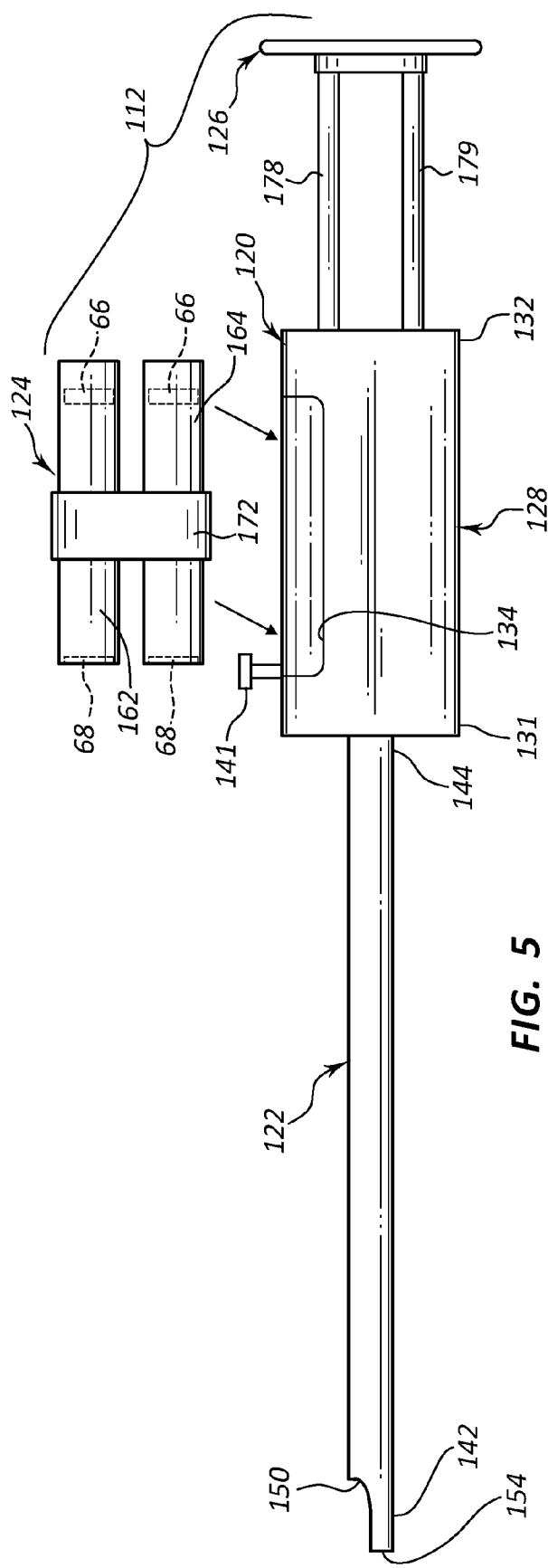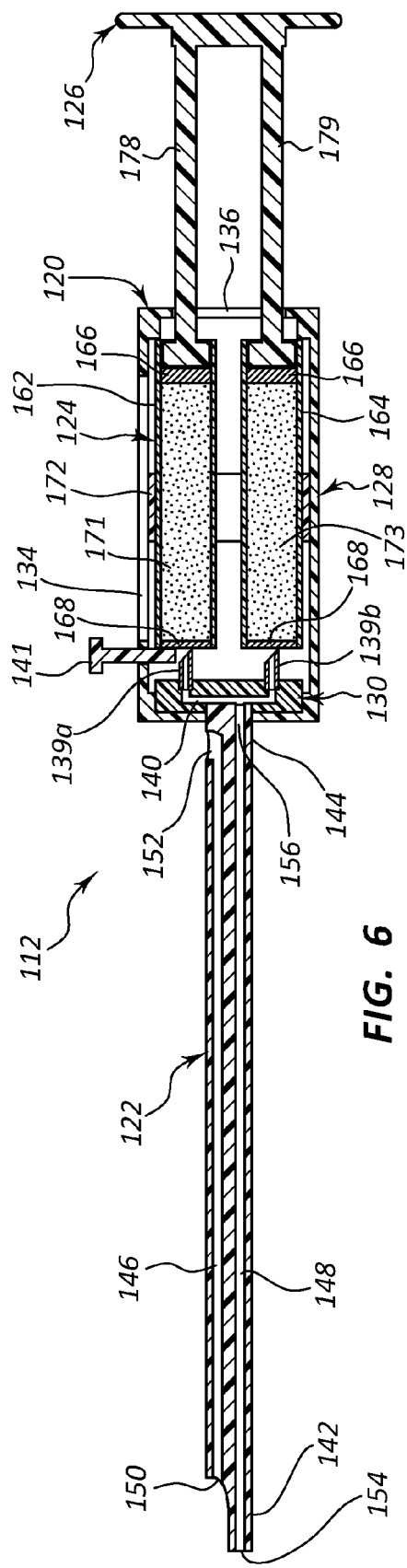

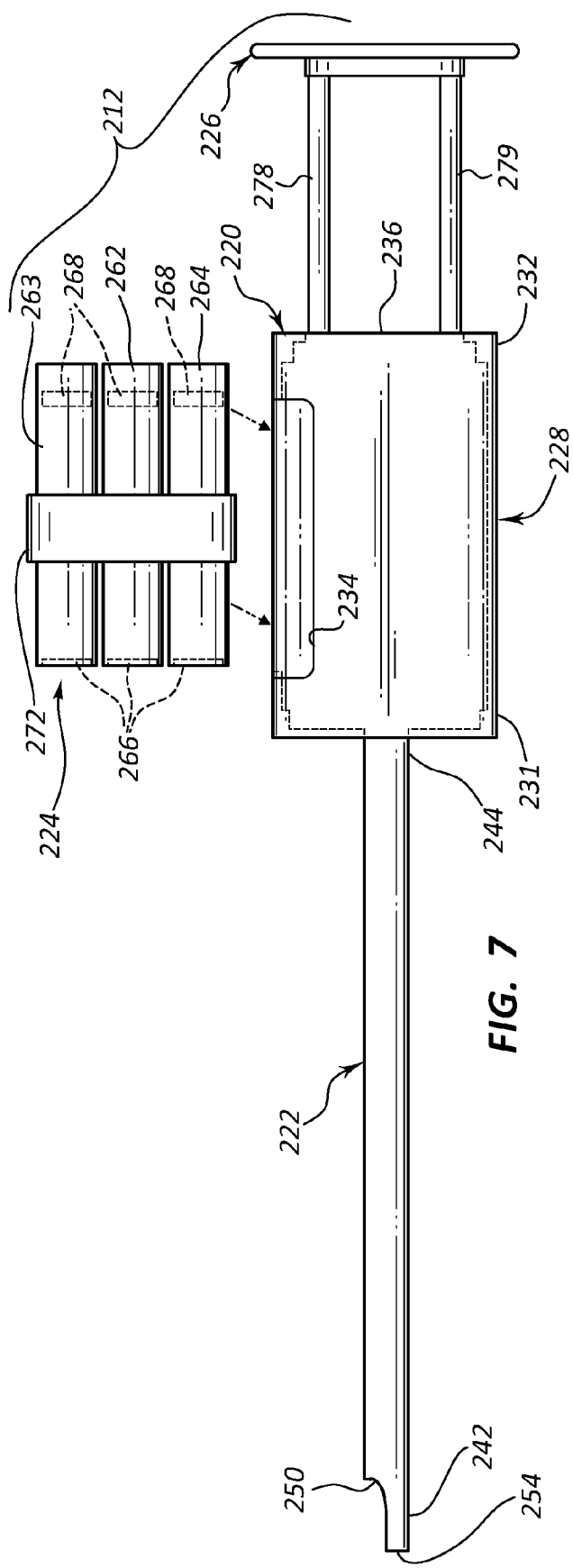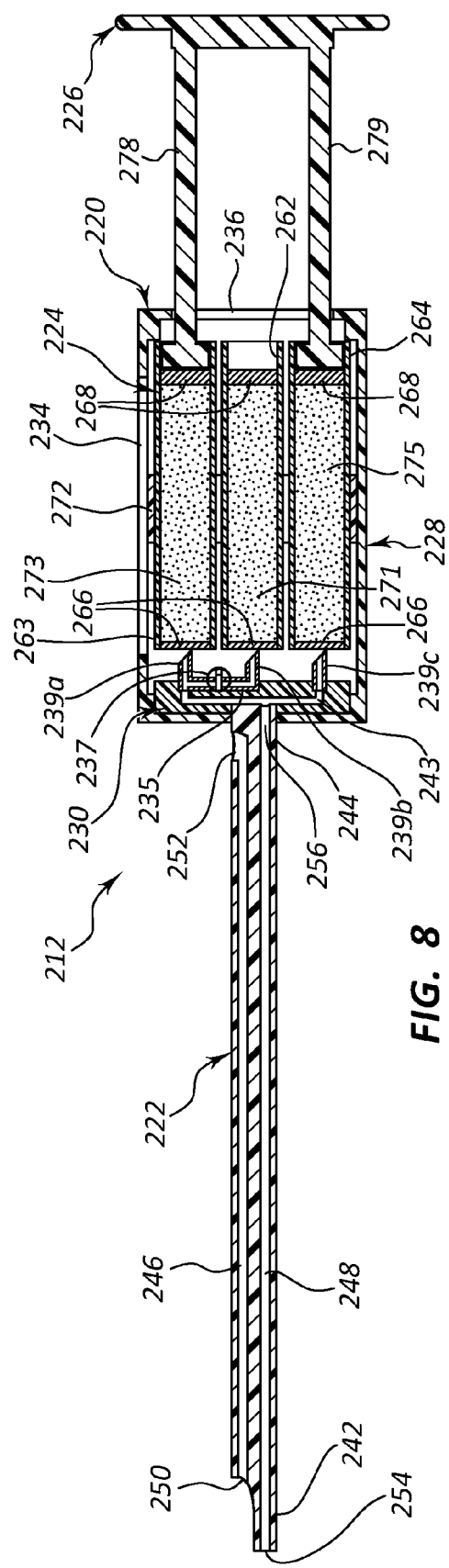

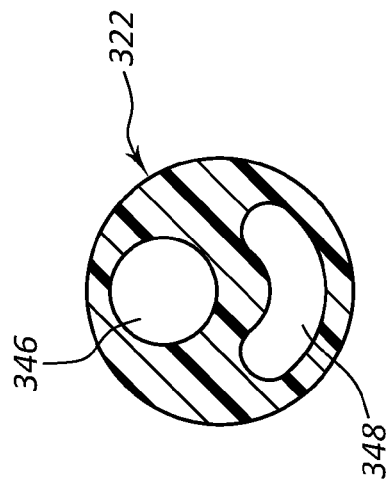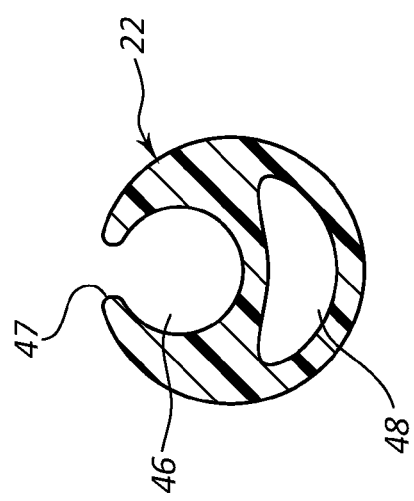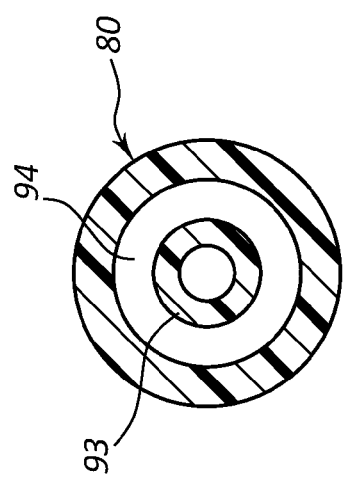
FIG. 9C
FIG. 9B
FIG. 9A

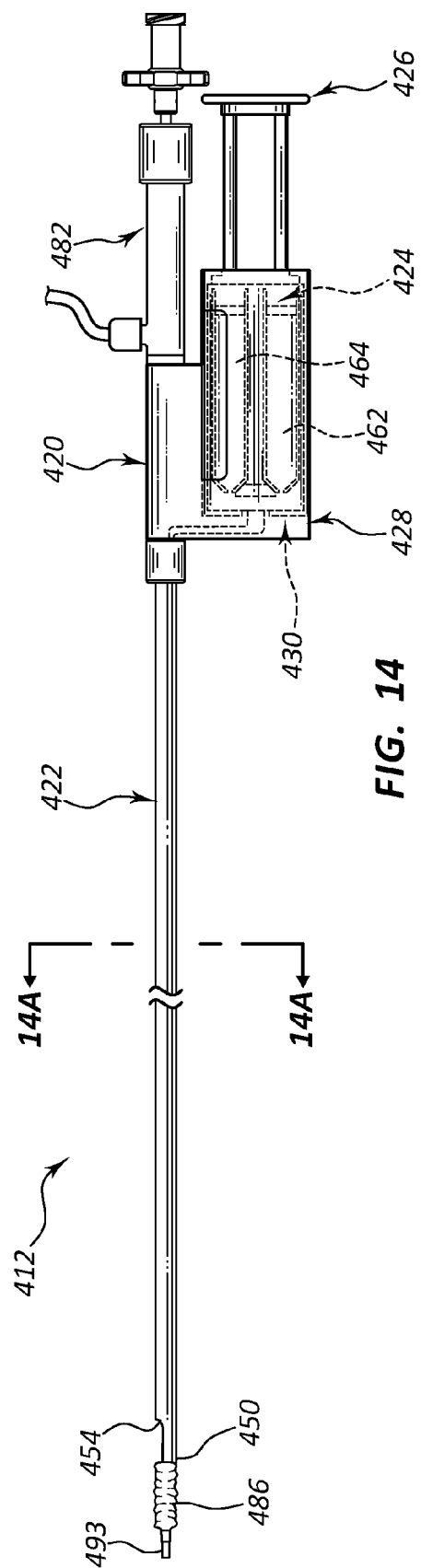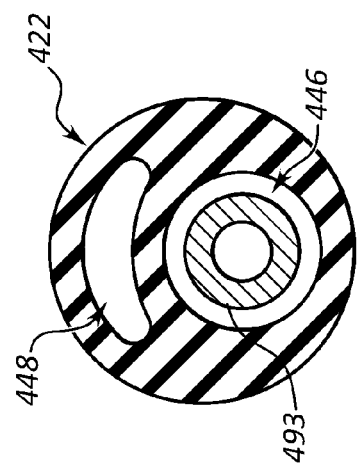
FIG. 14
FIG. 14A

BIOADHESIVE MIXING AND DELIVERY DEVICE AND METHODS

CROSS-REFERENCE TO RELATED APPLICATION

This application claims the benefit of the filing date of U.S. Provisional Application No. 61/693,052, filed Aug. 24, 2012, and entitled BIOADHESIVE MIXING AND DELIVERY DEVICE AND METHODS, the disclosure of which is incorporated, in its entirety, by reference.

TECHNICAL FIELD

The present disclosure relates generally to methods and systems for sealing tissue punctures, and more particularly, to methods and systems for mixing a bioadhesive sealant and delivering the mixed bioadhesive sealant to a tissue puncture.

BACKGROUND

Various surgical procedures are routinely carried out intravascularly or intraluminally. For example, in the treatment of vascular disease, such as arteriosclerosis, it is a common practice to access the artery and insert an instrument (e.g., a balloon or other type of catheter) to carry out a procedure within the artery. Such procedures usually involve the percutaneous puncture of the artery so that an insertion sheath may be placed in the artery and thereafter instruments (e.g., catheters) may pass through the sheath to an operative position within the artery. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, is typically stopped by utilizing vascular closure devices.

While there are a variety of prior art devices and techniques for closing such punctures, one primary problem is insuring a complete seal of the puncture. One technique includes the use of a bioadhesive material to seal the puncture. Some types of bioadhesive materials must be activated prior to use, and should be activated just prior to use in order to avoid premature activation of the bioadhesive material. The handling and activation of bioadhesive materials in applications related to vascular and other tissue puncture closure devices present a number of challenges, particularly when using bioadhesive sealant components that have a quick set time.

SUMMARY

One aspect of the present disclosure relates to a tissue puncture closure device that includes a delivery member, a handle assembly, and a sealant cartridge. The delivery member includes a sealant lumen and is insertable into a tissue puncture. The handle assembly is mounted to a proximal end of the delivery member and includes a cartridge chamber and a plunger member. The sealant cartridge is insertable into the cartridge chamber. The sealant cartridge has at least first and second sealant chambers carrying at least first and second sealant components, respectively. Operation of the handle assembly ejects the first and second sealant components into the sealant lumen for delivery to the tissue puncture.

The sealant cartridge may include first and second vials that define the first and second sealant chambers, respectively. The first and second vials are connected to each other. At least one of the first and second sealant chambers holds a vacuum pressure condition. The sealant cartridge may further include a third sealant cartridge carrying a third sealant component, and operation of the handle assembly mixes the first and third sealant components before ejecting the first and third sealant components into the sealant lumen.

The handle assembly may include a mixing chamber, wherein the first and second sealant components are mixed in the mixing chamber prior to being ejected into the sealant lumen. The tissue puncture closure device may include an ON/OFF valve configured to control flow of at least one of the first and second sealant components within the handle assembly. The handle assembly may include a plurality of needles arranged to pierce the cartridge upon operation of the plunger assembly. The first sealant component may include a powder and the second sealant component may include a liquid. The handle assembly may include a plunger, and operation of the handle assembly may include operating the plunger to eject the at least first and second sealant components.

Another aspect of the present disclosure relates to a handle assembly of a tissue puncture closure device. The handle assembly includes a housing, a plunger assembly, and a cartridge. The housing defines a cartridge chamber having a distal opening sized to receive a proximal end of a sealant delivery tube. The cartridge includes at least first and second sealant chambers carrying at least first and second sealant components, respectively. Operation of the plunger assembly ejects the first and second sealant components from the cartridge into the sealant delivery tube for delivery to a tissue puncture.

The cartridge may include a plurality of vials that define the first and second sealant chambers. The plurality of vials may be bound together as an assembly. The housing may include a lateral opening sized to receive the cartridge laterally into the housing. The housing assembly may include at least one ON/OFF valve that controls flow of the first and second sealant components within the housing. One of the first and second sealant chambers may hold a powder in a vacuum condition.

A further aspect of the present disclosure relates to a method of delivering a bioadhesive sealant for use in sealing a tissue puncture. The method includes providing a tissue puncture closure device having a sealant delivery tube, a handle assembly mounted to a proximal end of the sealant delivery tube, and a cartridge having at least first and second sealant chambers carrying first and second sealant components, respectively. The handle assembly includes a cartridge chamber. The method includes inserting the cartridge into the cartridge chamber, and operating the handle assembly to mix the first and second sealant components and eject the mixed sealant components into the sealant delivery tube for use in sealing a tissue puncture.

The first and second sealant components may be mixed prior to being ejected into the sealant delivery tube. The first and second sealant components may be mixed after being ejected from the cartridge. The sealant cartridge may include a mixing chamber, and operating the handle assembly mixes the first and second sealant components in the mixing chamber before ejecting the first and second sealant components into the sealant delivery tube. The method may include controlling flow of the at least one of the first and second sealant components with an ON/OFF valve within the handle assembly.

The foregoing and other features, utilities, and advantages of the invention will be apparent from the following detailed description of the invention with reference to the accompanying drawings.

BRIEF DESCRIPTION OF THE DRAWINGS

The accompanying drawings illustrate various embodiments of the present disclosure and are a part of the specification. The illustrated embodiments are merely examples of the present disclosure and do not limit the scope of the invention.

FIG. 5 is a partial exploded view of another example sealant delivery device in accordance with the present disclosure.

FIG. 6 is a cross-sectional view of the sealant delivery device of FIG. 5.

FIG. 7 is a partial exploded view of another example sealant delivery device in accordance with the present disclosure.

FIG. 8 is a cross-sectional view of the sealant delivery device of FIG. 7.

FIG. 9A is a cross-sectional view of a balloon inflation device of the vascular closure system of FIG. 9 taking along cross-section indicators 9A-9A.

FIGS. 9B and 9C are cross-sectional views of the sealant delivery device of the vascular closure system of FIG. 9 taking along cross-section indicators 9B,9C-9B,9C.

FIG. 14 shows an example balloon inflation device having features of the sealant delivery device of FIG. 9.

FIG. 14A is a cross-sectional view of the balloon inflation device of FIG. 14 taken along cross-section indicators 14A-14A.

Throughout the drawings, identical reference numbers designate similar, but not necessarily identical, elements.

DETAILED DESCRIPTION

Figure 1:
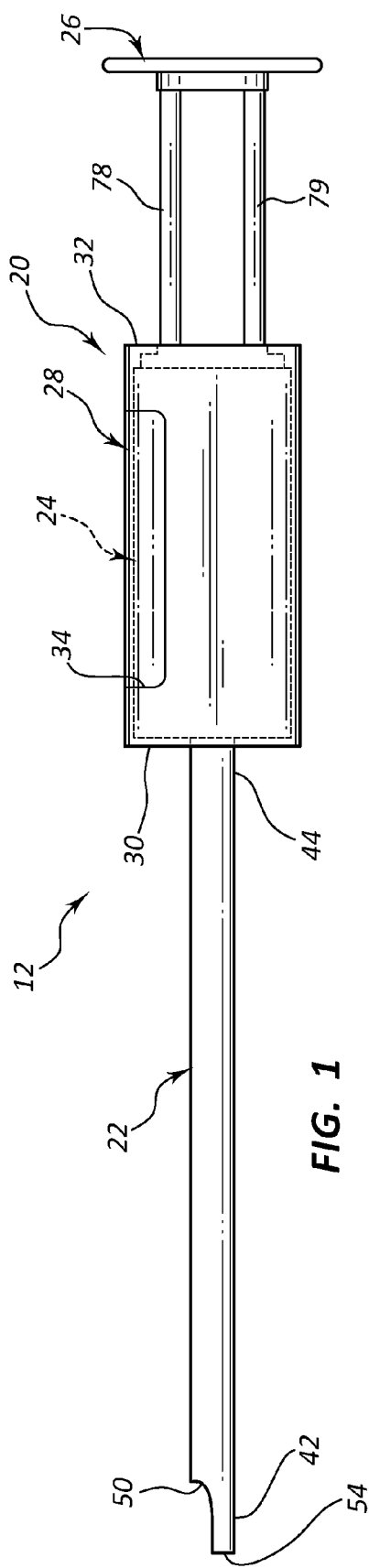
FIG. 1 is a side view of an example sealant delivery device in accordance with the present disclosure.

The systems disclosed herein may be used to close or seal percutaneous punctures made through the body tissue of a patient to gain access to a body cavity of a patient. Access through these percutaneous punctures allows a physician to carry out various procedures in or through the body cavity for examination, surgery, treatment and the like. While not meant to be limiting, the systems are illustrated being used to seal percutaneous punctures that provide access to blood vessels in patients for various procedures. It will be appreciated that the systems are applicable to other procedures requiring sealing of a puncture through body tissue into a cavity including, for example, laparoscopic surgery and other microscopic surgery techniques using a relatively small incision.

As used in this specification and the appended claims, the terms "engage" and "engagable" are used broadly to mean interlock, mesh, or contact between two structures or devices. Likewise "disengage" or "disengagable" means to remove or capable of being removed from interlock, mesh, or contact. A "tube" is an elongated device with a passageway. The passageway may be enclosed or open (e.g., a trough). A "lumen" refers to any open space or cavity in a bodily organ, especially in a blood vessel. The words "including" and "having," as well as their derivatives, as used in the specification, including the claims, have the same meaning as the word "comprising."

The general structure and function of tissue closure devices used for sealing a tissue puncture in an internal tissue wall accessible through an incision in the skin are well known in the art. Applications of closure devices including those implementing principles described herein include closure of a percutaneous puncture or incision in tissue separating two internal portions of a living body, such as punctures or incisions in blood vessels, ducts or lumens, gall bladders, livers, hearts, etc.

An exemplary embodiment of the present disclosure is directed to a vascular closure system that includes a sealant delivery device. The sealant delivery device may be configured to deliver a volume of flowable sealant such as a bioadhesive sealant to a tissue puncture to seal the tissue puncture. The sealant delivery device may include a handle assembly that is attached to a delivery tube. The delivery tube includes at least one lumen used to deliver the sealant to the tissue puncture. The handle assembly may be receptive of a sealant cartridge that carries at least one sealant component. In some arrangements, the sealant cartridge comprises a plurality of sealant components. The sealant components may remain separated from each other in the sealant cartridge until being ejected out of the sealant cartridge.

The sealant delivery device may include a cartridge connector assembly positioned within the handle. The cartridge connector assembly provides flow communication between the delivery tube and the cartridge. In one example, the cartridge connector assembly includes at least one connector seat such as a luer connector that receives a mating connecting feature of the sealant cartridge. In another example, the cartridge connector assembly includes at least one needle or other structure that breaks a seal of the sealant cartridge to provide the desired flow communication.

The handle assembly may also include an actuator such as a plunger assembly, which when actuated ejects the sealant components from a sealant cartridge. The actuator may be integrally formed with the handle assembly. Alternatively, the actuator assembly may be carried by the sealant cartridge or may be detachable from the handle assembly.

In some arrangements, the sealant cartridge is pre-packaged within the sealant delivery device. The sealant delivery device may include a slider or other structure that holds the sealant cartridge out of flow communication with the cartridge connector assembly during storage and delivery of the sealant delivery device for use with a patient. The slider may be actuated to permit flow communication of the sealant cartridge at the time of use. Alternatively, the sealant cartridge may be provided as an independent component of the sealant delivery device, which is inserted into the sealant delivery device as part of preparing the sealant delivery device for use. The sealant cartridge may include a plurality of individual containers (e.g., vials) that each hold a separate sealant component. The containers may be held together with a connector or positioned within a cartridge housing.

In one example, one of the sealant containers holds a sealant component under vacuum condition. Part of preparing the sealant for delivery may include providing flow communication between two or more of the sealant containers. The vacuum condition of one sealant container may automatically draw in the sealant component of another of the sealant containers, thereby mixing the sealant components of the two containers. Thereafter, operation of the actuator assembly may eject the mixed sealant components into the delivery tube. In one example, the sealant component stored under vacuum condition is a powder and the other sealant component is a liquid that is mixed with the powder.

The sealant delivery device may be used in combination with other features of the vascular closure system such as, for example, a balloon inflation device, a balloon location device, and a sheath. An example vascular closure system with which the sealant delivery devices disclosed herein may be used is described in U.S. Patent Application No. 61/693,148, filed on 24 Aug. 2012, and entitled "Balloon Bailout and Bioadhesive Delivery Device for Suture-Based Closure and Methods," which is incorporated herein in its entirety by this reference.

The sealant delivery device, including a handle assembly configured to receive a sealant cartridge, may be integrated into a balloon inflation device as will be described in further detail below. The sealant cartridge carries a plurality of sealant components in a modular, easy to handle construction, and may be inserted into a handle assembly. The use of a sealing cartridge may have certain advantages over types of sealant delivery systems that provide the sealant materials in different ways.

Referring now to FIGS. 1-4, an example sealant delivery device 12 is shown including a handle assembly 20, a delivery tube 22, a cartridge 24, and a plunger assembly 26. The sealant delivery device 12 may be referred to as a tissue puncture closure device or be part of a tissue puncture closure device or tissue puncture closure assembly. The handle assembly 20 is mounted to a proximal end of the delivery tube 22. The delivery tube 22 may include at least one lumen used to delivery a sealant to a tissue puncture. The delivery tube 22 may be referred to as a delivery device or a delivery member. The cartridge 24 is insertable into the handle assembly 20 in flow communication with a lumen of the delivery tube 22. The plunger assembly 26 may be used to eject sealant components held by the cartridge 24 into the lumen of the delivery tube 22.

Figure 2:
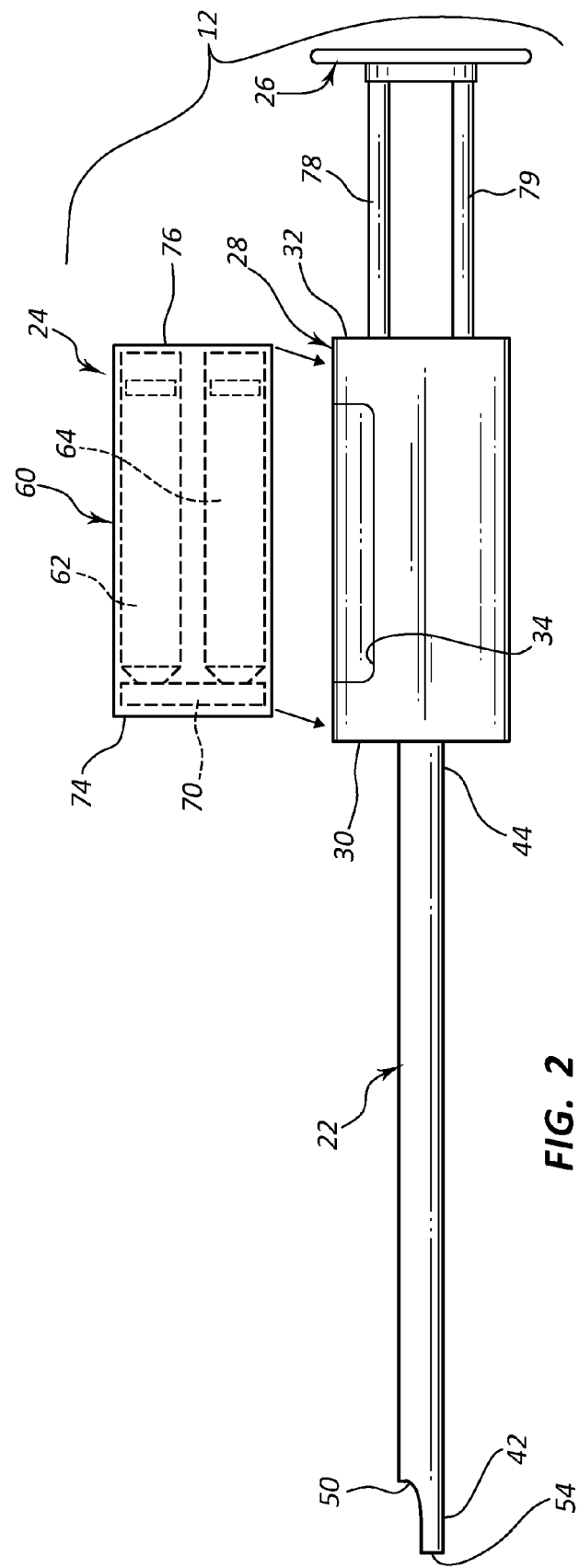
FIG. 2 is a partial exploded view of the sealant delivery device of FIG. 1.
Figure 3:
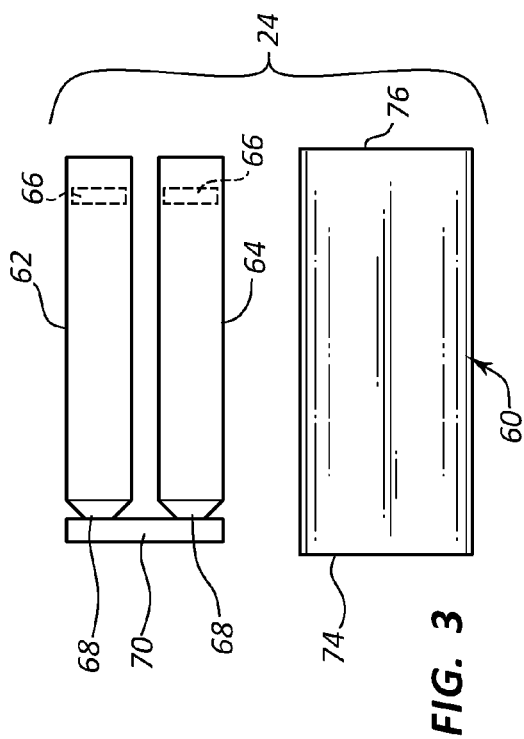
FIG. 3 is an exploded view of a sealant cartridge of the sealant delivery device of FIG. 1.

The handle assembly 20 may include a handle housing 28 and a cartridge connector assembly 30. The handle housing 28 includes distal and proximal ends 31, 32, a cartridge opening 34, and a plunger opening 36. The cartridge opening 34 may be formed in a sidewall along a length of the handle housing 28. Alternatively, the cartridge opening 34 may be formed at other locations such as along the proximal end 32 to provide a rear or axial insertion of the cartridge 24 into handle housing 28. FIG. 2 shows cartridge 24 being inserted laterally into handle housing 28 through a cartridge opening 34 formed in a sidewall at a location space between distal and proximal ends 31, 32.

Figure 4:
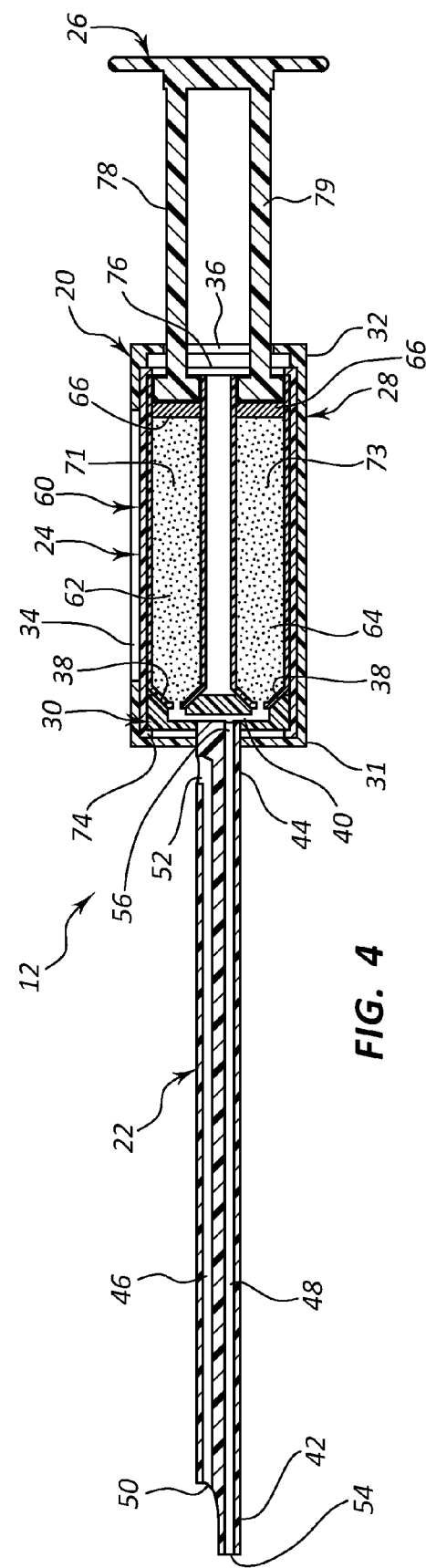
FIG. 4 is a cross-sectional view of the sealant delivery device of FIG. 1.

Cartridge connector assembly 30 may include a plurality of luer seats 38 and a channel 40 that is connected in flow communication with the delivery tube 22 (see FIG. 4). The luer seats 38 may be configured and arranged to connect with luer fittings of cartridge 24. The cartridge 24 may provide a fluid tight connection with the luer seats 38. Other types of cartridge connector assemblies 30 may be used to connect with cartridge 24. Likewise, cartridge 24 may have various types of connectors or fittings that provide a desired connection between the sealant components held by cartridge 24 and the delivery tube 22.

Delivery tube 22 may include distal and proximal ends 42, 44 and first and second lumens 46, 48. First lumen 46 may include distal and proximal openings 50, 52. Second lumen 48 may include distal and proximal openings 54, 56. First lumen 46 may be configured as a rapid exchange feature used to connect the sealant delivery device 12 to another device that is prepositioned within a tissue tract leading to a tissue puncture (e.g., see description below related to FIGS. 10-13). Distal and proximal openings 50, 52 may act as rapid exchange ports that provide connection of the delivery tube 22 to another structure such as a balloon inflation device or a guidewire.

Second lumen 48 may provide a pathway for delivery of the sealant carried by cartridge 24 to a tissue puncture. Distal opening 54 may deposit the sealant at the tissue puncture. Proximal opening 56 may be in flow communication with the cartridge 24 via the cartridge connector assembly 30.

Cartridge 24 includes a cartridge housing 60, first and second sealant containers 62, 64, a proximal seal 66, a distal fitting 68, and a cap 70. The first and second sealant containers 62, 64 may hold first and second sealant components 71, 73, respectively. The cartridge housing 60 may include a distal opening 74 and a proximal opening 76. The distal opening 74 may provide access to the first and second sealant containers 62, 64 for connection to the cartridge connector assembly 30. The proximal opening 76 may provide access for insertion of first and second plunger members 78, 79 of plunger assembly 26 into first and second sealant containers 62, 64 to force the first and second sealant components 71, 73 into the cartridge connector assembly 30 and delivery tube 22.

A proximal seal 66 may be positioned within each of the first and second sealant containers 62, 64 to help retain the first and second sealant components 71, 73 therein. The distal fitting 68 may be configured to meet with the luer seats 38 of cartridge connector assembly 30 to provide flow communication therebetween. Cap 70 may be connected to the distal fitting 68 during delivery and storage to help maintain a seal within the first and second sealant containers 62, 64. Cap 70 may be removed prior to inserting the cartridge 24 into handle housing 28. Cap 70 may help maintain the first and second sealant containers 62, 64 assembled together when removed from cartridge housing 60.

Actuating plunger assembly 26 (e.g., advancing the first and second plunger members 78, 79 distally relative to handle housing 28 and first and second sealant containers 62, 64) ejects the first and second sealant components 71, 73 into the cartridge connector assembly 30 and delivery tube 22. The first and second sealant components 71, 73 may at least partially mix within the channel 40 and second lumen 48 while being delivered to the distal opening 54 for deposit at the tissue puncture.

The sealants discussed herein may comprise a single component, or may comprise multiple sealant components that are mixed together. The multiple sealant components may further react together to form a crosslinked network. The sealant components may be naturally derived or synthetic. Some example synthetic components include polyethers such as polyethylene glycol, polypropylene glycol and polytetrahydrofuran. Other examples of synthetic components may include polyamine compositions such as polyvinylpyrrolidones, polyethylene imines and hydrogenated polyacrylonitriles. Other example sealant components include polyacrylic and methacrylic compounds such as polyacrylic acid. Example naturally derived components include protienaceous compositions such as albumin, collagen and polylysine. Other examples include carbohydrate compositions such polyhyaluronic acid. The sealant components may also contain reactive functional groups to promote chemical crosslinking The sealant components may be cross-linked by any known method including, for example, condensation reactions, Michael addition, and free radical. Functional groups used for cross-linking may include, for example, thiols, acrylates, amines, succinimydyls and aldehydes, to name a few.

In other arrangements, the first and second sealant containers may be connected together in a different way and have different constructions. Referring to FIGS. 5 and 6, another example sealant delivery device 112 includes a handle assembly 120, a delivery tube 122, a cartridge 124, and a plunger assembly 126. The cartridge 124 includes first and second sealant containers 162, 164 that are connected together with a connecting member 172. The connecting member 172 may include, for example, an elastic material, band, strap, etc., which retains the first and second sealant containers 162, 164 together. Each of the first and second sealant containers may include a proximal seal 166 and a distal seal 168. The distal seal 168 may include a puncturable material through which a needle may be advanced to gain access to first and second sealant components 171, 173, respectively. The first and second sealant containers 162, 164 may include glass or polymer vials or other containers having other relatively rigid materials.

The cartridge 124 is insertable into a handle housing 128 of a handle assembly 120. The handle housing 128 includes distal and proximal ends 131, 132, a cartridge opening 134, and a plunger opening 136. The handle assembly 120 may include a cartridge connector assembly 130 having a channel 140 and a pair of needles 139a,b. The needles 139a,b are connected in flow communication with the channel 140. The channel 140 is connected in flow communication with a lumen of the delivery tube 122.

Delivery tube 122 may include first distal and proximal ends 142, 144 and first and second lumens 146, 148. The first lumen 146 may include distal and proximal openings 150, 152. Second lumen 148 may include distal and proximal openings 154, 156. First lumen 146 may provide a rapid exchange connection with another device as described above with reference to first lumen 46. The second lumen 148 may provide a fluid channel for delivery of a sealant from the cartridge 124 to a vessel puncture.

The cartridge 124, when inserted laterally into handle housing 128 via cartridge opening 134, may be arranged such that the distal seals 168 are aligned with the needles 139a,b. The distal seals 168 may be held spaced apart from the needles 139a,b by a slider 141. Slider 141 may be used to hold the cartridge 124 out of contact with the cartridge connector assembly 130 until the sealant delivery device 112 is ready for use. Removing or actuating the slider 144 may permit axial movement of the first and second sealant containers 162, 164 so that needles 139a,b pierce the distal seals 168.

The first and second sealant containers 162, 164 may be advanced distally by advancing first and second plunger members 178, 179. In some arrangements, advancing first and second plunger members 178, 179 may apply a distally directed force to proximal seals 166 that causes the needles 139a,b to pierce the distal seals 168. In other arrangements, the distal seals 168 may be pierced by the needles 139a,b as part of inserting the cartridge 124 into the handle housing 128. The use of slider 141 may be particularly helpful when pre-mounting cartridge 124 within handle housing 128 prior to shipping and storage of sealant delivery device 112.

Further advancing the first and second plunger members 178, 179 may force the first and second sealant components 171, 173 through the cartridge connector assembly 130 and into the second lumen 148 of delivery tube 122 and eventually out of the distal opening 154 for use in sealing a tissue puncture.

Referring now to FIGS. 7 and 8, another example sealant delivery device 212 includes similar features as the sealant delivery device 112, but may be configured to accommodate at least three sealant containers. Sealant delivery device 212 includes a handle assembly 220, a delivery tube 222, a cartridge 224, and a plunger assembly 226. The handle assembly 220 includes a handle housing 228 and a cartridge connector assembly 230. Handle housing 228 includes distal and proximal ends 231, 232, a cartridge opening 234, and a plunger opening 236. Cartridge connector assembly 230 includes a mixing chamber 243, a plurality of needles 239a-c, and an ON/OFF valve 237.

The needles 239a,b may be connected with an intermediate channel 235 (see FIG. 8). The ON/OFF valve 237 may be positioned along the intermediate channel 235 to control fluid flow between the needles 239a,b.

Delivery tube 222 includes distal and proximal ends 242, 244, and first and second lumens 246, 248. The first lumen 246 includes distal and proximal openings 250, 252. Second lumen 248 includes distal and proximal openings 254, 256. First lumen 246 may provide a rapid exchange connection to another device as described above with reference to first lumen 46. Second lumen 248 may be connected in flow communication with the mixing chamber 243 of cartridge connector assembly 230.

Cartridge 224 may include first, second and third sealant containers 262, 263, 264, proximal seals 266, and distal seals 268. The first, second and third sealant containers 262-264 may be connected together with a connecting member 272. The first, second and third sealant containers 262-264 may hold first, second and third sealant components 271, 273, 275, respectively.

In one example, the first sealant container 262 includes the first sealant component 271 in a liquid form. The second sealant container 263 holds second sealant component 273 in a powder form. The second sealant component is held under a vacuum pressure condition. Initially, the ON/OFF valve 237 is operated to an ON or open position such that needles 239a,b are connected to flow communication. When the needles 239a,b pierce the distal seals 268 of the first and second sealant containers 262, 263, the vacuum pressure within second sealant container 263 draws the first sealant component 271 into the second sealant container 263 to mix with the second sealant component 273. The ON/OFF valve is then actuated to the OFF or closed position. Further actuating the plunger assembly 226 to eject the sealant components from the cartridge 24 includes ejecting the mixture of first and second sealant components 271, 273 from the second sealant container 263 and into the mixing chamber 243 to mix with the third sealant component 275, which is being ejected from the third sealant container 264. The first, second and third sealant components 271, 273, 275 continue to mix in the mixing chamber 243 and second lumen 248 as they are delivered to the tissue puncture.

Other arrangements are possible for sealant delivery devices in accordance with the present disclosure to include cartridges carrying four or more sealant containers and four or more sealant components. Any desired number of sealant containers or a single sealant container including multiple chambers that carry different sealant components may be used as part of a sealant cartridge carried by handle assembly. In some arrangements, multiple cartridges may be inserted into a single handle assembly.

Figure 9:
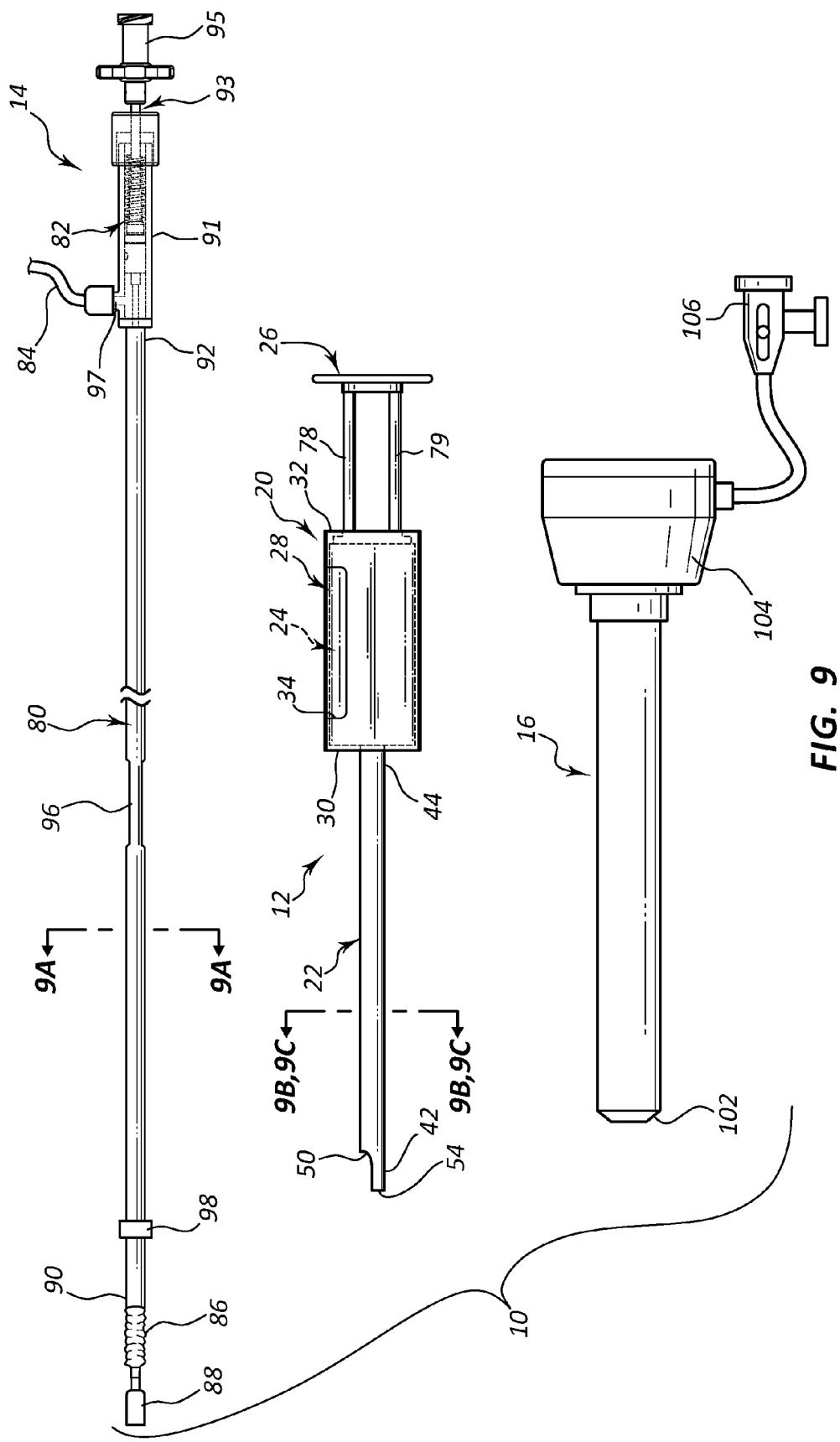
FIG. 9 is a side view of an example vascular closure system including the sealant delivery device of FIG. 1.

Referring now to FIG. 9, an example vascular closure system 10 is shown including the sealant delivery device 12, a balloon inflation device 14, and a sheath 16. FIG. 9B shows a cross-section of sealant delivery device 12. The first lumen 46 may include a side opening 47 that provides lateral access to the first lumen. Side opening 47 may assist in mounting the sealant delivery device 12 to the balloon inflation device 14. FIG. 9C shows an alternative construction for a delivery tube 322 having a first lumen 346 that is closed around its periphery, and a second lumen 348. Either of the delivery tube constructions shown in FIGS. 9B and 9C may be used for the sealant delivery device 12.

The balloon inflation device 14 includes an inflation tube 80, a balloon location device 82, an inflation source 84, a balloon 86, and a detachable tip 88. The inflation tube 80 may include distal and proximal ends 90, 92, an inflation lumen 94, an exchange port 96, and a collar 98 (see FIGS. 9 and 9A). Balloon location device 82 may include a housing 91, an inner tube 93, an inner tube manifold 95, and an inflation port 97. The inner tube 93 may extend through the inflation lumen 94 of the inflation tube 80 to a location distal of the distal end 90 of inflation tube 80. Balloon 86 may be coupled at its proximal end to the inflation tube 80 and connected at its distal end to inner tube 93. Inner tube 93 may move axially relative to housing 91 upon inflation of balloon 86 to provide a visual indicator to the operator of a condition of the balloon 86 (e.g., an inflation pressure or a size of balloon 86). Detachable tip 88 may be connected at a distal end of inner tube 93.

Sheath 16 may include a distal end 102, a hub 104, and an injection port 106. In operation, the balloon inflation device 14 is advanced through the sheath 16, and the balloon inflation device 14 and sheath 16 are advanced through a tissue track to a tissue puncture. In a later step, the sealant delivery device 12 may be advanced along the balloon inflation device 14 to the tissue puncture for delivery of a sealant carried by cartridge 24 to seal the tissue puncture.

Figure 10:
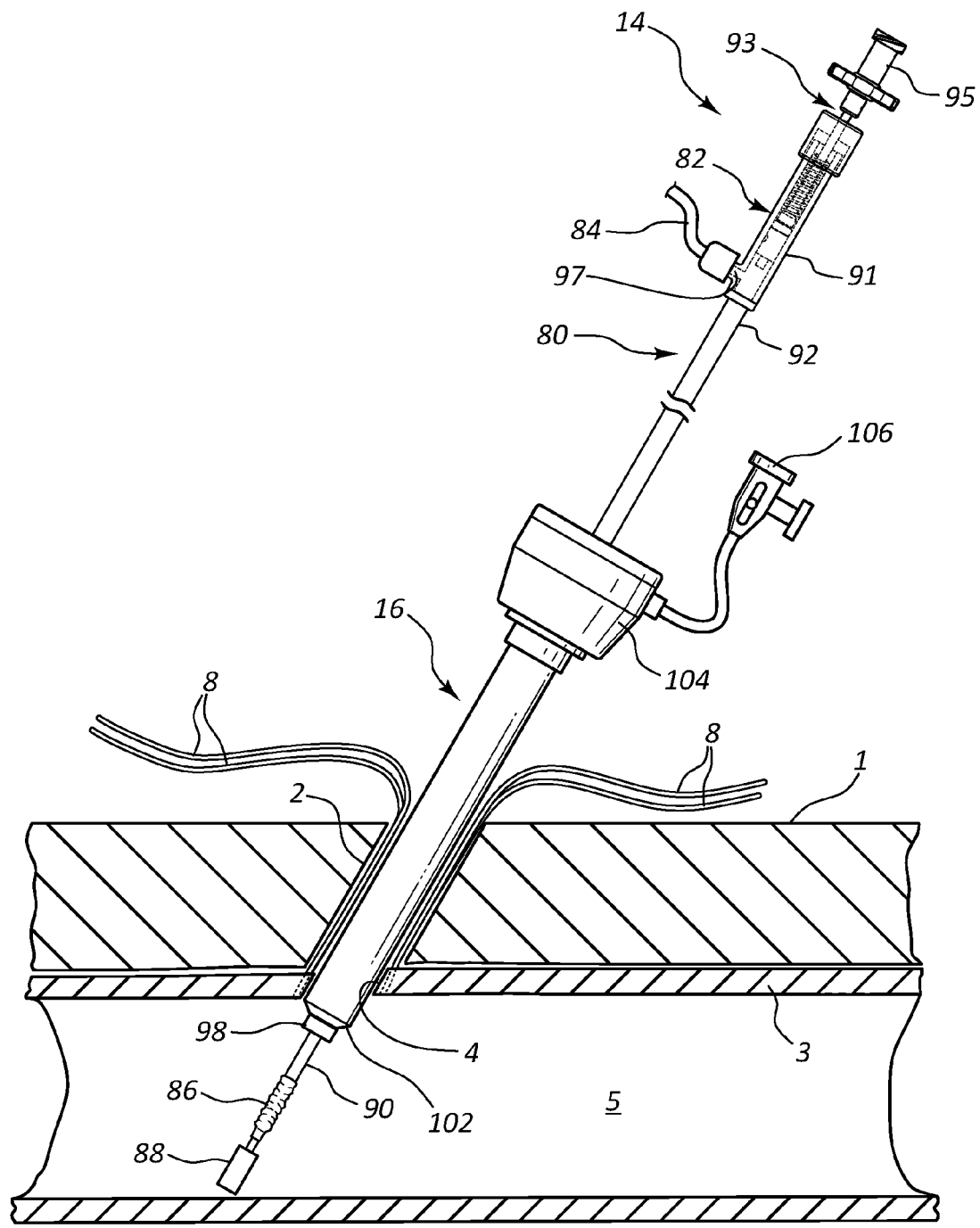
FIGS. 10-13 illustrate steps of using the vascular closure system of FIG. 9 to seal a vessel puncture.
Figures 11, 11A:
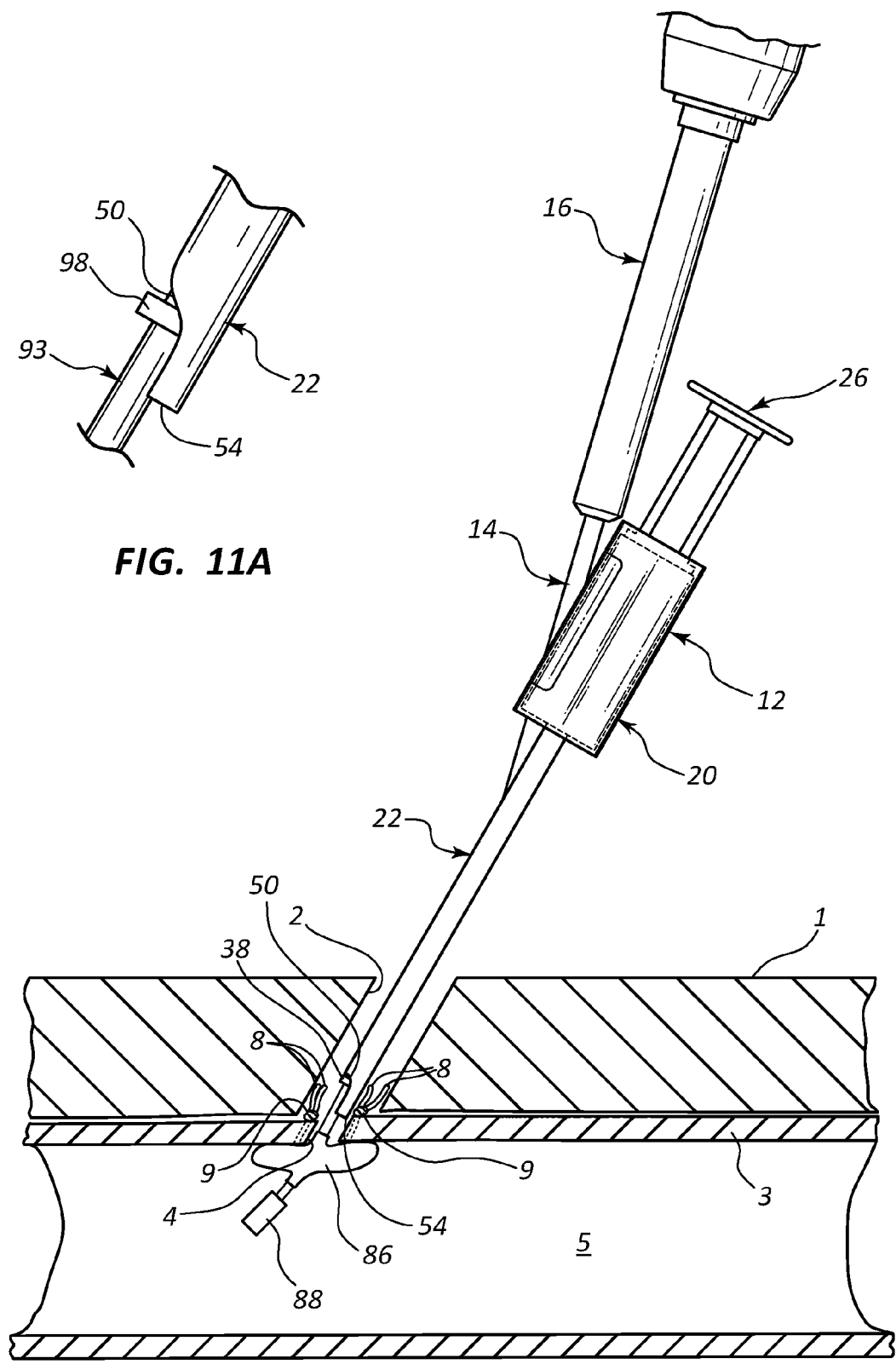

Referring now to FIGS. 10-13, example steps for sealing enclosed a tissue puncture using vascular closure system 10 are shown and described. FIG. 10 shows balloon inflation device 14 and sheath 16 being advanced through a tissue tract 2 of a tissue layer 1 and through a vessel puncture 4 to a vessel interior 5. In some arrangements, at least one suture 8 is positioned extending through a wall of vessel 3 prior to advancing balloon inflation device 14 and sheath 16 through the vessel puncture 4. The balloon 86 is then inflated via the inflation source 84 and drawn into contact with an inner surface of vessel 3 adjacent to vessel puncture 4 (see FIG. 11). The inflated balloon 86 provides a temporary seal of the vessel puncture 4 and may also act as an anchor and reference point for operation of other functions of vascular closure system 10.

Sheath 16 may be withdrawn proximately along balloon inflation device 14 so that the sealant delivery device 12 may be inserted through the tissue tract 2. In at least one example, the sealant delivery device 12 is mounted to the balloon inflation device 14 at the exchange port 96. The sealant delivery device 12 may be advanced distally along the balloon inflation device 14 to position the distal opening 54 adjacent to vessel puncture 4. A collar 98 may act as a position stop to position distal opening 54 at a location spaced proximal of the vessel puncture 4 so that the sealant delivered by sealant delivery device 12 may flow more freely into tissue tract 2 and vessel puncture 4.

Figure 12:
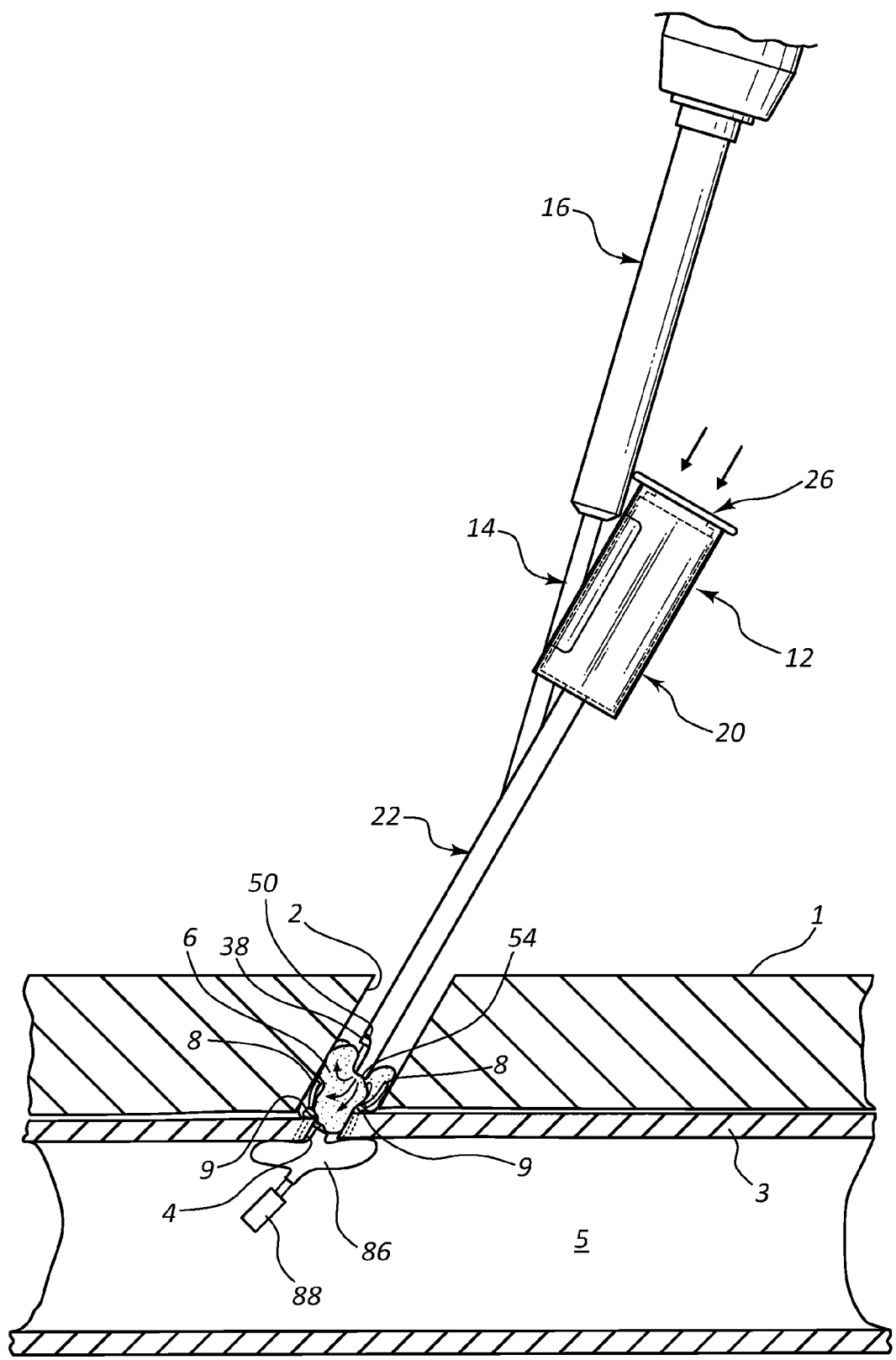
Figure 13:
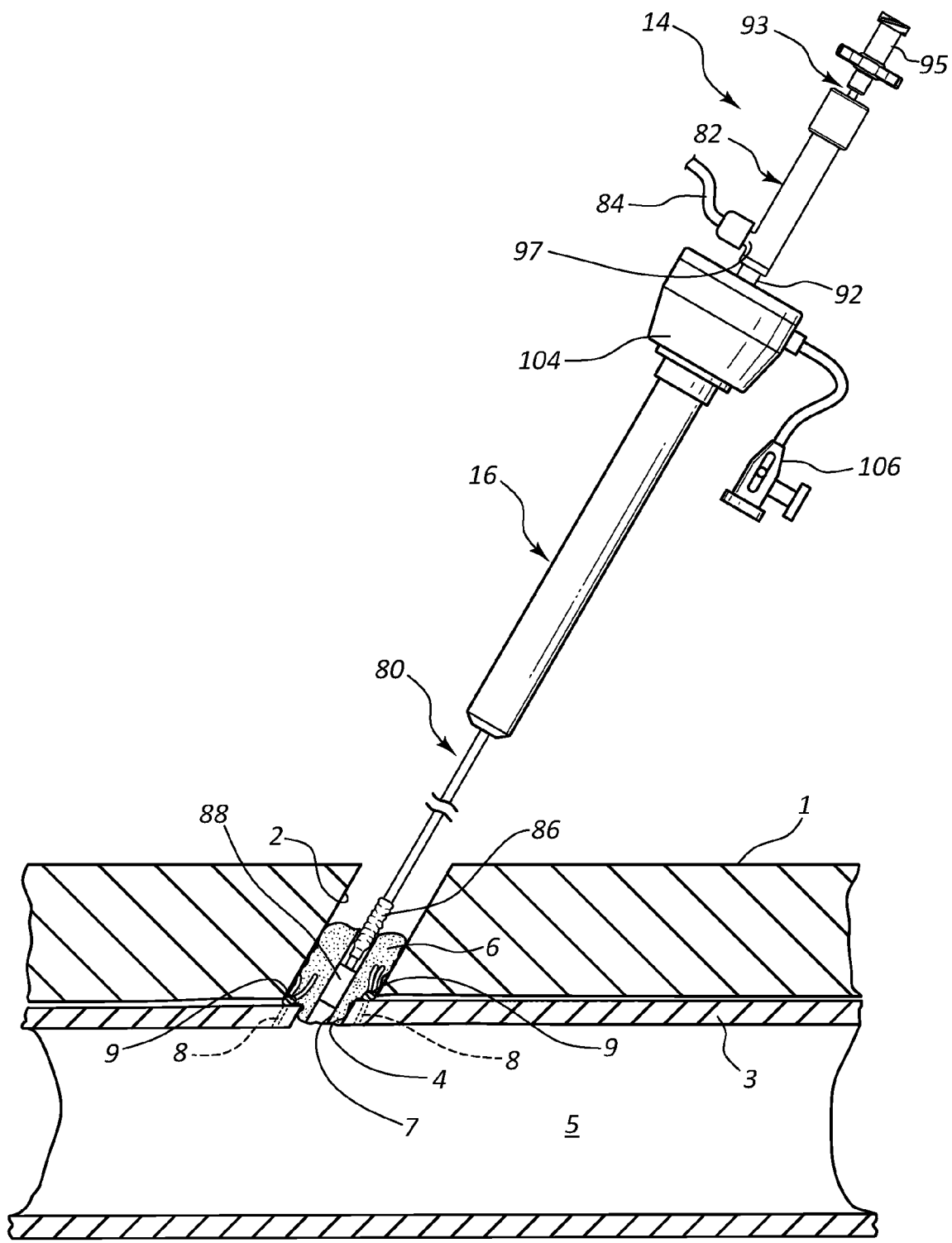

Referring to FIG. 12, the plunger assembly 26 is operated to advance the sealant carried by cartridge 24 through delivery tube 222 and out of distal opening 54 to fill the tissue tract 2 and vessel puncture 4. The sealant may form a sealant plug 6 (see FIG. 13).

The sealant delivery device 12 may be withdrawn, the balloon 86 deflated, and the balloon inflation device 14 withdrawn to position the detachable tip 88 within a plug channel 7 formed in sealant plug 6. The detachable tip 88 may be detached and lodged within sealant plug 6 to further seal vessel puncture 4 and tissue tract 2. In some arrangements, a secondary volume of sealant may be deposited in tissue tract 2 proximal of sealant plug 6. The secondary sealant may be delivered via the balloon inflation device 14 (e.g., via the inner tube 93) or using the sealant delivery device 12.

Referring now to FIGS. 14 and 14A, some features of the balloon inflation device 14 may be integrated into a sealant delivery device 412. Sealant delivery device 412 may include a handle assembly 420, a delivery tube 422, a cartridge 424, and a plunger assembly 426. The sealant delivery device 412 may also include a balloon location device 482, a balloon 486 and an inner tube 493. The inner tube 493 may extend through the delivery tube 422. The balloon 486 may be connected to at least one of the delivery tube 422 and the inner tube 493.

Handle assembly 420 may include a handle housing 428 and a cartridge connector assembly 430 having any of those features of the cartridge connector assemblies described herein. Delivery tube 422 may include first and second lumens 446, 448, that include distal openings 450, 454, respectively. Cartridge 424 may include at least first and second sealant containers 462, 464. Cartridge connector assembly 430 may provide flow communication between the first and second sealant containers 462, 464 and the second lumen 448. Operating the plunger assembly 426 ejects sealant components carried by the first and second sealant containers 462, 464 through the cartridge connector assembly 430 and second lumen 448 to be expelled at the distal opening 454 to help seal a vessel puncture.

Many types of handle assembly and cartridge designs may be used with sealant delivery device 412. Sealant delivery device 412 may be configured to hold cartridges having at least one sealant container. The cartridge may be integrally formed with the sealant delivery device to form an arrangement that may be disassembled. In other arrangements, the cartridge may be provided separate from the handle assembly 420 and moved into and out of the handle assembly either laterally or longitudinally.

The plunger assemblies disclosed herein may have various constructions. In at least one example, the handle assembly has integrated into it a trigger or other actuator that performs the plunging functions described herein.

The preceding description has been presented only to illustrate and describe exemplary embodiments of the invention. It is not intended to be exhaustive or to limit the invention to any precise form disclosed. Many modifications and variations are possible in light of the above teaching. It is intended that the scope of the invention be defined by the following claims.

What is claimed is:

1. A tissue puncture closure device, comprising:
   a delivery member having a sealant lumen and being insertable into a tissue puncture;
   a handle assembly mounted to a proximal end of the delivery member, the handle assembly comprising a cartridge chamber and a plunger member, a proximal seal coupled to the plunger member;
   a sealant cartridge insertable into the cartridge chamber, the sealant cartridge having at least first and second sealant chambers carrying at least first and second sealant components, respectively;
   wherein operation of the handle assembly ejects the at least first and second sealant components into the sealant lumen for delivery to the tissue puncture.

2. The tissue puncture closure device of claim 1, wherein the sealant cartridge includes first and second vials that define the at least first and second sealant chambers, respectively.

3. The tissue puncture closure device of claim 2, wherein the first and second vials are connected to each other.

4. The tissue puncture closure device of claim 1, wherein at least one of the at least first and second sealant chambers hold a vacuum pressure condition.

5. The tissue puncture closure device of claim 1, wherein the sealant cartridge further includes a third sealant cartridge carrying a third sealant component, and operation of the handle assembly mixes the at least first and third sealant components before ejecting the at least first and third sealant components into the sealant lumen.

6. The tissue puncture closure device of claim 1, wherein the handle assembly includes a mixing chamber, and the at least first and second sealant components are mixed in the mixing chamber prior to being ejected into the sealant lumen.

7. The tissue puncture closure device of claim 1, further comprising an ON/OFF valve configured to control flow of at least one of the at least first and second sealant components within the handle assembly.

8. The tissue puncture closure device of claim 1, wherein the handle assembly further includes a plurality of needles arranged to pierce the sealant cartridge upon operation of the handle assembly.

9. The tissue puncture closure device of claim 1, wherein the first sealant component comprises a powder and the second sealant component comprises a liquid.

10. The tissue puncture closure device of claim 1, wherein the handle assembly includes a plunger, and operation of the handle assembly includes operating the plunger to eject the at least first and second sealant components.

* * * * *